(12) United States Patent
Chen et al.

(10) Patent No.: US 10,869,725 B2
(45) Date of Patent: Dec. 22, 2020

(54) SIMULATED METHOD AND SYSTEM FOR NAVIGATING SURGICAL INSTRUMENT BASED ON TOMOGRAPHY

(71) Applicants: China Medical University, Taichung (TW); China Medical University Hospital, Taichung (TW)

(72) Inventors: Yi-Wen Chen, Taichung (TW); Cheng-Ting Shih, Taichung (TW); Wei-Chuan Chen, Taichung (TW)

(73) Assignees: China Medical University, Taichung (TW); China Medical University Hospital, Taichung (TW)

( * ) Notice: Subject to any disclaimer, the term of this patent is extended or adjusted under 35 U.S.C. 154(b) by 209 days.

(21) Appl. No.: 15/701,510

(22) Filed: Sep. 12, 2017

(65) Prior Publication Data
US 2018/0199998 A1 Jul. 19, 2018

(30) Foreign Application Priority Data
Jan. 13, 2017 (TW) .............................. 106101315 A (51) Int. Cl.
*A61B 34/20* (2016.01)
*A61B 34/10* (2016.01)
(Continued)

(52) U.S. Cl.
CPC ............ *A61B 34/20* (2016.02); *A61B 5/0536* (2013.01); *A61B 6/022* (2013.01); *A61B 6/12* (2013.01);
(Continued)

(58) Field of Classification Search
None
See application file for complete search history.

(56) References Cited

U.S. PATENT DOCUMENTS

| 2004/0102698 A1* | 5/2004 | Vilsmeier | ............... A61B 5/06 600/424 |
| 2012/0071890 A1* | 3/2012 | Taylor | ............... A61B 5/6817 606/129 |

(Continued)

OTHER PUBLICATIONS

J. Hoffmann et al. "Craniofacial Endosseus Implant Positioning With Image-Guided Surgical Navigation". Perspective in Image-Guided Surgery, pp. 137-143 (2004).*

*Primary Examiner* — Serkan Akar
*Assistant Examiner* — Jillian K. McGough
(74) *Attorney, Agent, or Firm* — Alan D. Kamrath; Karin L. Williams; Mayer & Williams PC (57) ABSTRACT

A simulated method and system for surgical instrument based on tomography are provided. The method includes obtaining a biological stereoscopic image and inputting a parameter set of an implant to be implanted, denoting a target position and an initial position in the biological stereoscopic image, estimating a dimensional coordinate of a contact area of the implant and a living organism when the implant has been implanted into the living organism based on the parameter set, the target position and the initial position in the biological stereoscopic image, and obtaining a physiological data set by re-sampling corresponding to the dimensional coordinate of the implant in the living organism for evaluating the effect after the implant has been implanted into the living organism. Surgeons may evaluate the effect after implantation of implant into the living organism by using the simulated method, enhancing the overall quality and result of the surgery.

2 Claims, 6 Drawing Sheets

(51) Int. Cl.

| | |
|---|---|
| *G06T 19/00* | (2011.01) |
| *G06F 3/0481* | (2013.01) |
| *G06F 3/0484* | (2013.01) |
| *A61B 6/02* | (2006.01) |
| *H04N 13/204* | (2018.01) |
| *A61B 6/12* | (2006.01) |
| *A61B 6/03* | (2006.01) |
| *A61B 8/08* | (2006.01) |
| *A61B 90/00* | (2016.01) |
| *H04N 13/00* | (2018.01) |

(52) U.S. Cl.
CPC .......... *A61B 34/10* (2016.02); *G06F 3/04815* (2013.01); *G06F 3/04847* (2013.01); *G06T 19/003* (2013.01); *H04N 13/204* (2018.05); *A61B 6/032* (2013.01); *A61B 8/085* (2013.01); *A61B 2034/2051* (2016.02); *A61B 2034/2055* (2016.02); *A61B 2034/2065* (2016.02); *A61B 2090/3762* (2016.02); *H04N 2013/0074* (2013.01)

(56) References Cited

U.S. PATENT DOCUMENTS

| | | | |
|---|---|---|---|
| 2014/0044768 A1* | 2/2014 | Lin | A61K 31/28 424/422 |
| 2014/0236159 A1* | 8/2014 | Haider | A61B 17/1626 606/88 |
| 2016/0191887 A1* | 6/2016 | Casas | H04N 13/296 348/47 |
| 2016/0324598 A1* | 11/2016 | Bothorel | A61B 34/20 |

\* cited by examiner

SIMULATED METHOD AND SYSTEM FOR NAVIGATING SURGICAL INSTRUMENT BASED ON TOMOGRAPHY

FIELD OF THE INVENTION

The present invention relates to a simulated method and system for surgical operation, and more particularly to a simulated method and system for surgical instrument navigation based on tomography.

BACKGROUND OF THE INVENTION

In today's medical surgeries, implantations of implants, such as bone screws and catheters, into human body are involved. Surgical qualities of these highly depend on Computed Tomography and X-ray photography. Taking spinal surgery as an example, in which spinal fusion is a common clinical spinal fixation/correction surgery, mostly for the treatment of posterior lumbar spine, scoliosis and degenerative disc disease, in order to reduce abnormal vertebral body movement, compression, and thereby improving and curing patients having back pain or neurological deficits. In this instance, during spinal fusion surgeries, a bone screw must be drilled along the pedicle into the vertebrae to achieve the purpose of spinal correction through fixation or pull-to-center of the screw. In this kind of surgeries, the bone screw implantation path, the bone volume fraction of the contact area of the bone screw and the vertebrae, and the volume density of the bone directly affect the quality and result of the operation. Therefore, the position and angle of penetrating the bone screw is critical. In current clinical practice, most of the positioning and navigation of the bone screws are performed and assisted by utilizing computed tomography or fluoroscopy, in which the position and angle of penetrating the bone screws have to be determined by the surgeons based on preoperative analyses and their own experiences. However, the image obtained from fluoroscopy is a two-dimensional projected image, which is difficult to precisely estimate the depth position in its natural anatomical structure. Besides, this kind of surgical operation is irreversible because it is destructive to the human body tissue, and is unlikely to be re-operated once the postoperative evaluation result of the surgery is negative.

Therefore, in current surgical knowledge and techniques, the surgeons are only able to rely on their own clinic experiences in conjunction with computed tomography or X-ray photography of the patient while performing the surgeries; it is hard to carefully evaluate the path of implanting and the spatial distribution of the implant and physiological parameters of the patient after puncturing the implant, which subsequently causes difficulties for the pre-operative assessment and the follow-on implementation surgery.

SUMMARY OF THE INVENTION

In view of the fact that existing tomography and x-ray photography are not yet sufficient to assist in preoperative evaluation of implantation surgeries and real-time navigation (navigation) during such surgeries, a method and system for navigating surgical instrument based on tomography is provided To achieve the above aspect, a simulated method for navigating surgical instrument based on tomography is provided and includes:

obtaining a biological stereoscopic image and inputting a parameter set of an implant to be implanted;

denoting a target position and an initial position in the biological stereoscopic image;

estimating a dimensional coordinate of a contact area of the implant and a living organism when the implant has been implanted into the living organism based on the parameter set, the target position and the initial position in the biological stereoscopic image;

obtaining a physiological data set by re-sampling corresponding to the dimensional coordinate of the implant in the living organism for evaluating the effect after the implant has been implanted into the living organism.

The simulated method of the present invention for navigating surgical instrument based on tomography can simulate the position of the implant to be implanted before the implant is implanted into the living organism, as well as the contact area of the implant with the living organism after the implantation, the surgeons can use this to evaluate whether the implantation path meets the expected effect, and to evaluate whether the implant penetrates vital organs or tissues, thereby improving the quality of the operation and the effect of the treatment, and avoiding harming the vital organs and tissues in the living organism.

To achieve the above aspect, a simulated system for navigating surgical instrument based on tomography is provided and includes:

a biological stereoscopic image capture device for obtaining a biological stereoscopic image;

a scan positioning device for tracking a position of an implant to be implanted in order to denote an initial position;

an input unit for inputting a parameter set of the implant and denoting a target position;

a processor, connected to the biological stereoscopic image capture device, the scan positioning device, and the input unit, wherein the processor receives, processes, and outputs the biological stereoscopic image, the position of the implant, the parameter set, the target position and the initial position to obtain a physiological data set of a contact area of the implant and the living organism;

a display, connected to the processor for displaying the physiological data set.

BRIEF DESCRIPTION OF THE DRAWINGS

The structure and the technical means adopted by the present invention to achieve the above and other objects can be best understood by referring to the following detailed description of the preferred embodiments and the accompanying drawings.

DETAILED DESCRIPTION OF THE PREFERRED EMBODIMENTS

The structure and technical features of the present invention will now be described in considerable detail with reference to some embodiments and the accompanying drawings thereof, so that the present invention can be easily understood.

Figure 1:
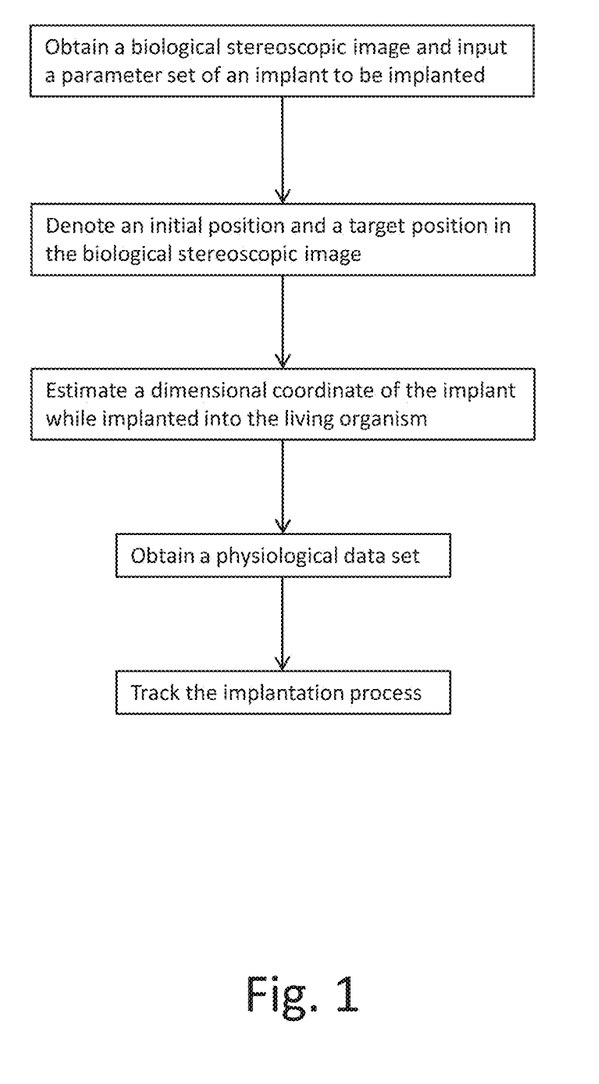
FIG. 1 is a flowchart of the present invention.

Referring to FIG. 1, a simulated method for navigating surgical instrument based on tomography according to the present invention includes:

obtaining a biological stereoscopic image and inputting a parameter set of an implant to be implanted, in which the biological stereoscopic image may be an image obtained through computed tomography, magnetic resonance imaging, X-ray stereoscopic modeling etc., and the parameter set may include the length, volume, stereoscopic image, weight, density, weight distribution, material, etc., of the implant;

denoting a target position (position to place the implant) and an initial position (initial position of the implant) in the biological stereoscopic image, in this instance, the implant can be tracked by a scan positioning device utilizing, for instance, infrared or laser stereoscopic positioning techniques for positioning the implant, in which users may obtain the parameter set of the appearance information of the implant (ex. length, diameter, outline, etc.) by registering the implant in the scan positioning device, then, the implant may be displaced in the living organism to be implanted in order to denote the initial position by the scan positioning device, when the initial position has been denoted, the target position may be set by an input unit, in which the target position is where the implant is to be placed in the living organism, alternatively, the target position may also be set by referring to the initial position and the parameter set (length) of the implant, where the position and the path of implanting the implant in the living organism may also be determined when the initial position and the target position have been determined;

estimating a dimensional coordinate of a contact area of the implant and a living organism when the implant is implanted into the living organism based on the parameter set, the target position and the initial position in the biological stereoscopic image;

obtaining a physiological data set by re-sampling corresponding to the dimensional coordinate of the implant in the living organism for evaluating the effect after the implant has been implanted into the living organism. In the step of obtaining the physiological data set, different manners are used depending on the materials set in the parameter set of the implant according to the present embodiment; details will be set forth below.

Figure 2A:
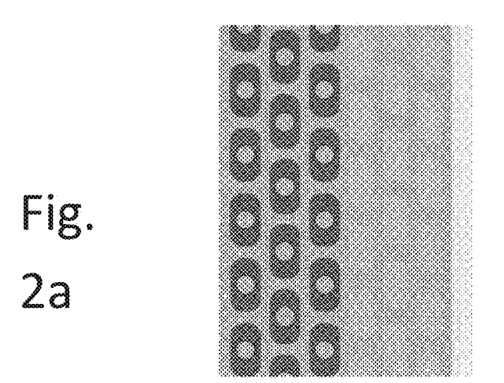
FIGS. 2a to 2c are schematic diagrams illustrating two operational modes for obtaining physiological data set.
Figure 2B:
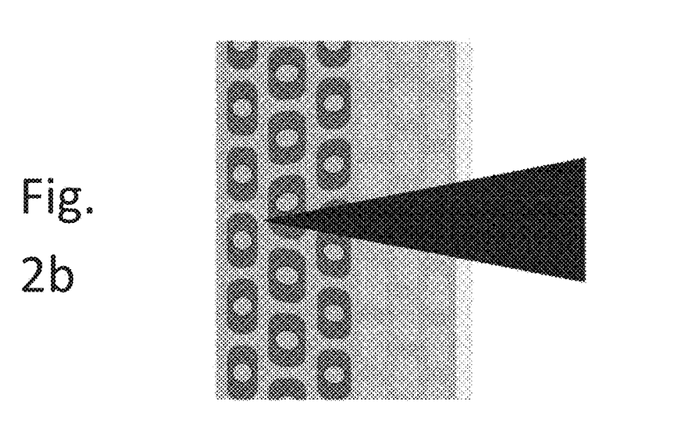
Figure 2C:
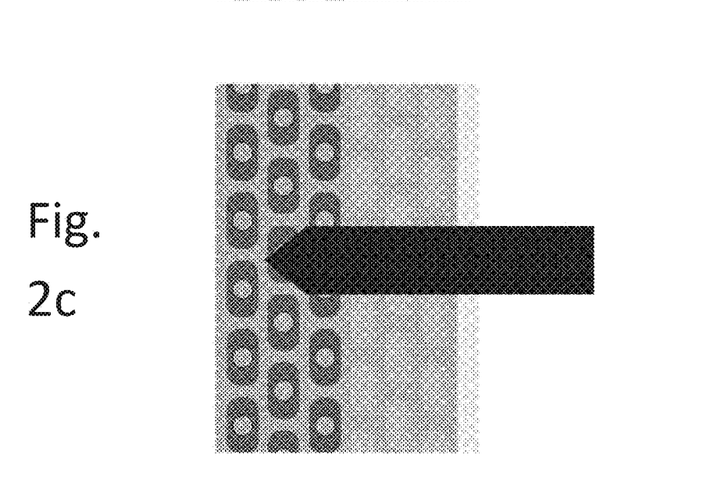

Because that implantation surgeries can be majorly classified into two types of destructive operations, rigid and soft, thus, a rigid destructive mode and a soft destructive mode are provided in the present invention, which can be selected by the users (surgeons) while setting the parameter set of the implant; the physiological data set and the contact area of the implant and the living organism are obtained and estimated by different ways depending on the material used. Referring to FIG. 2a and FIG. 2c, during rigid destructive operations, the space of the original tissue is replaced by the implant (see FIG. 2c, the implant replaces the orginial tissue in FIG. 2a), under this scenario, the physiological data set corresponding to the dimensional coordinate can be easily obtained by simply sampling the corresponding space where the original tissue is to be replaced by the implant, in order to estimate the contact area of the implant and the living organism. Now refer to FIG. 2a and FIG. 2b, during soft destructive operations, the original tissue will be pushed to the sides while being cut or punctured by surgical instruments (see FIG. 2b, the implant pushes the original tissue in FIG. 2b), under this scenario, the contact area of the implant and the tissue in the living organism would be the tissue being pushed aside, and that the deformation of the tissue in the biological stereoscopic image has to be calculated according to the parameter set of the implant before the sampling, in order to correctly obtain the dimensional coordinate and the corresponding physiological data set.

Figure 3A:
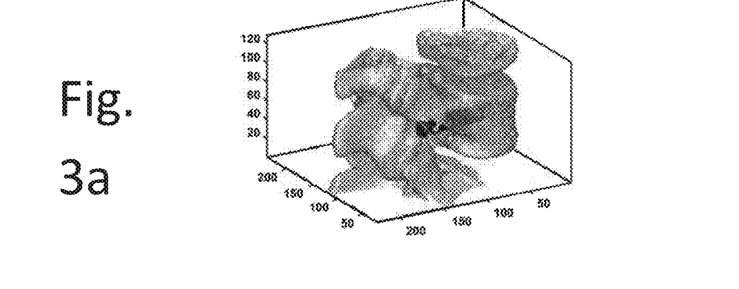
FIG. 3a depicts a dimensional coordinate obtained by a step illustrated in FIG. 1.
Figure 3B:
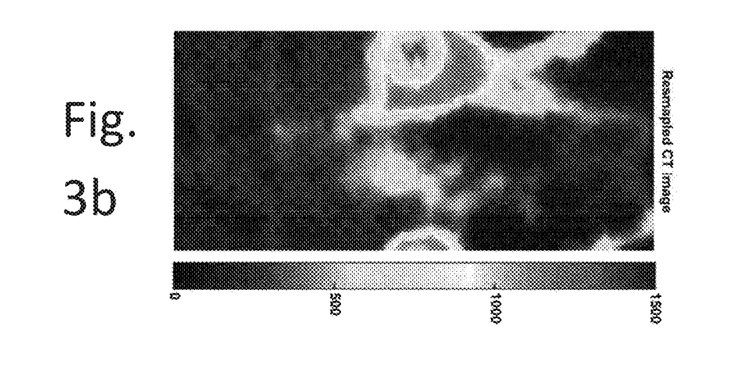
FIGS. 3b to 3d are physiological data sets obtained by a step illustrated in FIG. 1.
Figure 3C:
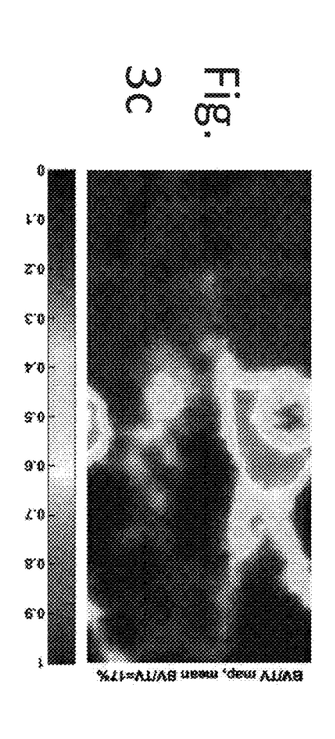
Figure 3D:
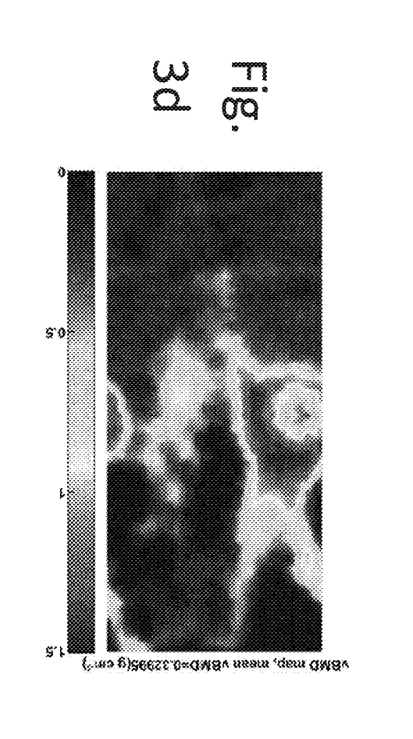

Further refer to FIG. 3a illustrating an exemplary embodiment of implanting a bone screw, after processing through the above steps of setting the target position and the initial position, a virtual implant can be displayed in the biological stereoscopic image, where the dimension coordinate of the contact area of the virtual implant and the living organism can be calculated and obtained, such that the contact area of the implant and the living organism can be anticipated. The aforementioned step of re-sampling is to re-sample the position corresponding to the dimensional coordinate in the living organism based on computed tomographical scanning, alternatively MRI scanning or other infrared scanning means are also applicable, thereby obtaining the physiological data set corresponding to the dimensional coordinate as shown in FIG. 3b (CT scan/image), in which the CT scan may be further converted into bone volume fraction (bone volume/total volume, BV/TV) illustrated in FIG. 3c, and volumetric bone mineral density (vBMD) illustrated in FIG. 3d.

Since the CT values are derived from the attenuation coefficient representing the level of X-ray attenuation by the tissue, it is directly proportional to the physical density of the tissue, as most bone density measurement techniques simply classify bone structure into cortical bone and bone marrow, CT values can be converted into bone volume fraction (BV/TV) and volumetric bone mineral density (vBMD) by using a known combination of cortical bone marrow equivalent prostheses as a reference standard with quantitative CT or a two-compartment model (TCM) of a conventional technique. For instance, while converting CT values into bone physiological parameters, the aforementioned TCM model may be applied to obtain bone volume fraction and volumetric bone mineral density, in which only one simple standard sample is needed as a reference to obtain those bone physiological parameters from the CT values by the aforementioned step. Besides, human bone structure is usually considered as two main kinds of tissue compositions in general scientific researches or clinical practices, i.e. osteon and bone marrow, while using quantitative CT as an instance, after homogenizing materials having similar photon attenuation characteristics of the two respective tissue compositions in different proportions (by using either potassium hydrogen phosphate DAP or hydroxyl apatite HAP as an analogy of osteons, and distilled or distilled deionized water as an analogy of bone marrow can be), an equivalent bone material may be produced for simulating different bone densities, and since the mixing ratio of these prostheses is already known, the CT values can be obtained directly from the CT scan. Thus, the CT values of practical CT images only need to be compared and interpolated with the CT values of these equivalent prostheses to convert CT values into equivalent bone density of the bone material.

The physiological data set obtained by the above steps can be used by the surgeons to assess the amount of the bone contacting the bone screw, thereby further evaluating the mechanical factors and stability of the bone screw implanted. In addition, the number of trabeculae is closely related to the stability of the implanted bone screw, mechanical relational function between the bone volume fraction and the stability of the bone screw may be established by using bones. The average bone volume fraction/volume bone density value obtained from the CT image of the contact area can be referenced as an indication of the stability of the bone screw while being implanted under the implantation path, which can be used for clinical assessment.

Figure 4A:
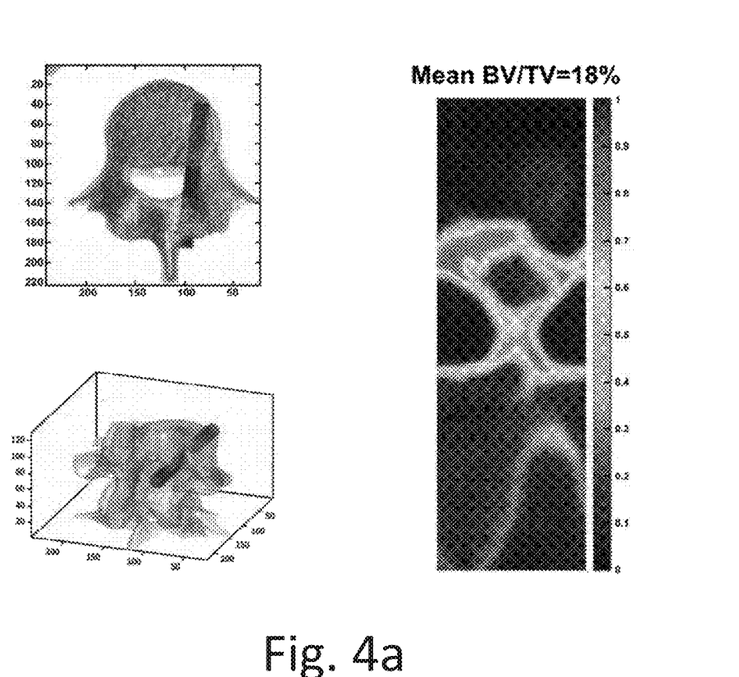
FIGS. 4a and 4b are physiological data sets and dimensional coordinates of another embodiment obtained by a step illustrated in FIG. 1.
Figure 4B:
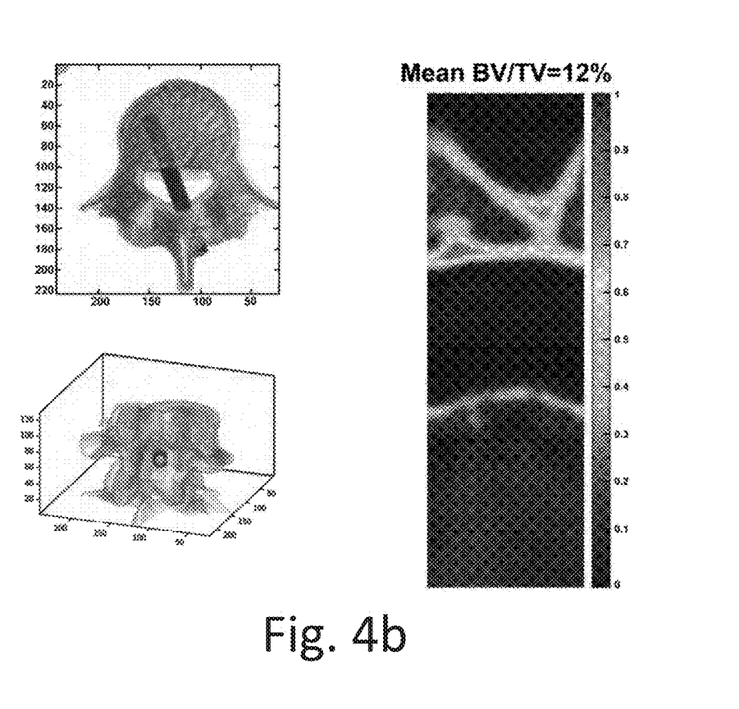

Further refer to FIG. 4a to FIG. 4b, when the users operate the input device for displacing the virtual implant in the living organism, the contact area between the virtual implant and the living body will change constantly, and the dimensional coordinate can therefore be constantly tracked and the physiological data set corresponding to the new dimensional coordinates can be updated (CT scans are used as examples in the figures), so that the surgeons can observe the contact of the implant with the living organism to fine-tune the implantation angle.

The present invention can also be applied to visceral catheter implantation or punch biopsy procedures, according to the present embodiment, while capturing the biological stereoscopic image (ex. CT image), physiological data set such as blood vessel path of a contact area can be developed in the CT image by using contrast agent, the blood flow of these blood vessels can also be known with the use of developing agent and phantom in conjunction with a two-component model, in order to see if the catheter is in contact with or penetrated through important blood vessels. For instance, in punch biopsy surgeries, if the important blood vessels are not intended to be punctured, only the positions of the catheter and the blood vessels are needed to be known. Contrarily, if the blood vessels are intended to be punctured, for instance, while performing an angiography, the position of the blood vessels can be found by using the above steps for assisting on the puncture. Additionally, for liver donors, the cutting site can be determined based on the distribution of blood vessels before laparotomy.

Figure 5A:
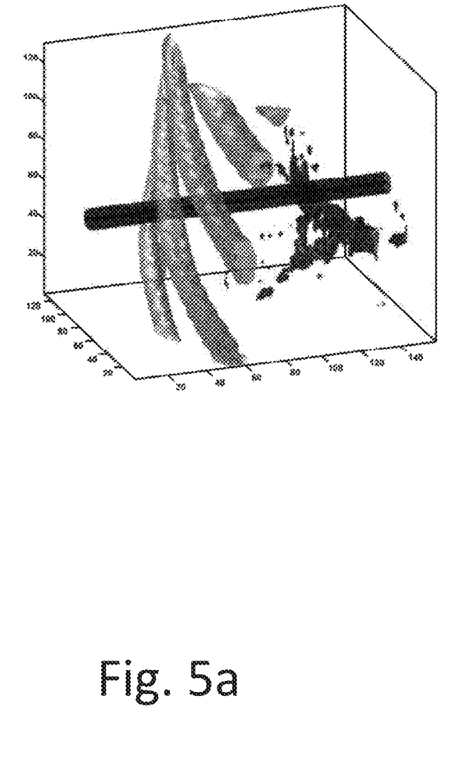
FIG. 5a depicts another dimensional coordinate obtained by a step illustrated in FIG. 1.
Figure 5B:
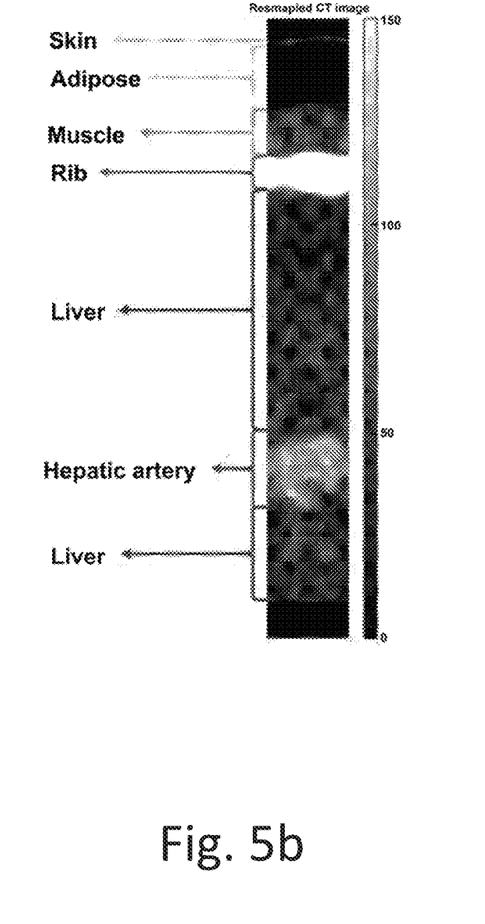
FIG. 5b depicts another physiological data set obtained by a step illustrated in FIG. 1.

Please refer to FIG. 5a and FIG. 5b, according to the present embodiment, using liver biopsy as an exemplary instance, while capturing biological stereoscopic images (for example, CT images), the developing agent is injected intravenously into the living organism prior to capturing liver artery CT images. FIG. 5a shows the position of the puncture needle in the dimensional coordinate of the living organism, and FIG. 5b shows the physiological data set of the CT images of the contact area of the puncture needle and the living body. The surgeons can thereby know the puncture path from the skin, fat, muscle, rib, liver and the hepatic artery developed via developing agent and the distribution and proportion, to see whether the puncture path is proper.

The aforesaid biological stereoscopic image may be a CT image, an MRI image, or an X-ray stereoscopic image, etc., which may be selected depending on the surgical requirements or may be synthesized by a plurality of images, in which while MRI images are used, specific imaging signals, such as diffusion-weighted images, elasticity-factor images and MR angiography, which is generated by the pulse sequence used for MRI imaging, may also be used to image the contact area having different physiological parameters, to provide references for clinical assessments, such as whether the catheter is properly placed at the cerebral hemorrhage or infarct location, and whether the spine is in contact with the spinal nerve, vertebral artery, and so on.

After completion of the implantation path assessment, in order to further track whether the implantation path of the implant conforms to the planned implantation path, scan positioning devices can be used to position the surgical instrument (implant). According to the present embodiment, the positioning is done by completely scanning the entire implant or capturing the positioning points (Red dots) on the implant, so that the system can track the spatial location of the implant in the living organism by the scan positioning device, and by using a positioned CT scan obtained through a C-Arm or O-arm CT scanner, the implant in the scanning range can be depicted in the image, so that the operator, namely the surgeon, can instantaneously understand the relative position of the surgical instrument (implant) in the living organism anatomy, i.e. human anatomy, by observing the position of the surgical instrument in the image.

Figure 6:
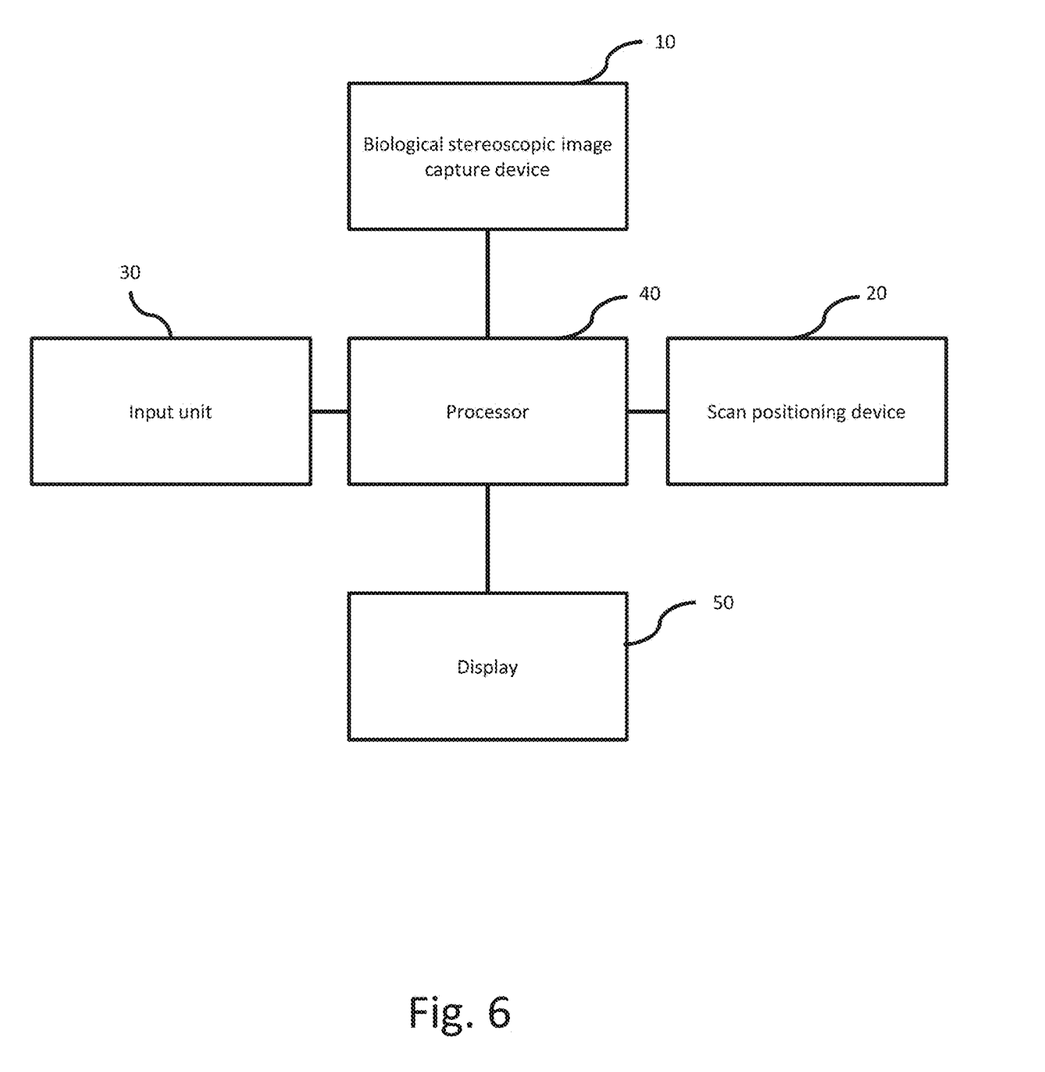
FIG. 6 is a block diagram illustrating the simulated system of the present invention.

Referring to FIG. 6, to bring the aforementioned simulated method for navigating surgical instrument based on tomography to practice, a system for executing the simulated method is also provided by the present invention which includes:

a biological stereoscopic image capture device 10 for obtaining a biological stereoscopic image, and, practically, can be performed through computed tomography or magnetic resonance imaging techniques;

a scan positioning device 20 for tracking a position of an implant to be implanted in order to denote an initial position, in this embodiment, the scan positioning device can be an infrared or a laser stereoscopic positioning device;

an input unit 30 for inputting a parameter set of the implant and denoting a target position;

a processor 40, connected to the biological stereoscopic image capture device 10, the scan positioning device 20, and the input unit 30, in which the processor receives, processes, and outputs the biological stereoscopic image, the position of the implant, the parameter set, the target position and the initial position to obtain a physiological data set of a contact area of the implant and the living organism;

a display 50, connected to the processor for displaying the physiological data set.

While practically embodying the above mentioned simulation method and system based on a tomographic image in surgical operations, a portable computer tomography (CT) or intraoperative CT are used to obtain CT images of the patients supine or prone on the operating table, and then the surgical instruments will be positioned by infrared or laser stereotactic techniques and registered in the system, in which the appearance information of different kinds of surgical instruments (implants) can be pre-operatively registered in the system. Alternatively, the surgical instruments can also be positioned and registered intraoperatively by an infrared positioning device or laser stereotactic techniques provided by the system. As a result, the system may continuously track the dimensional coordinates and orientation by learning the outlines of the surgical instruments. The present invention uses positioning information of surgical instruments to generate the system vector needed for sampling the contact area image, and can use the appearance information, including shapes etc., of the contact area to generate the dimensional coordinate information of the sampled contact area image, so that the surgeon can evaluate whether the position and angle of the surgical instrument registered in the system meets the anatomy of the patient's anatomical structure prior to the drilling, screwing or placing the catheter, the implantation path and orientation may also be instantaneously monitored during the surgical operation. Therefore, in spinal fusion procedures, the precision of bone screw implantation can be improved, the time of surgery and anesthesia can be shortened, and the wound size may be miniaturized so that the recovery time needed is also shortened, thereby improving the quality of surgery. In addition, the present invention can also be widely applied to catheter and puncture surgeries as well as most of the common clinical surgeries to enhance the quality of surgeries and the effect of treatment, and to avoid harming vital organs and tissues in a living organism.

It is also worth to be mentioned that the invention may not only be applied to navigating surgical instruments by showing real-time simulated images of the contact area for precise implantation, but also applicable to pre-operation assessments for various objectives. For instance, the present invention may be used as a reference for planning the implantation or puncturing path of implants, and for designing follow-on surgical guides as well. The present invention is fully applicable to various objectives once a tomographic image is obtained.

Although the present embodiments and their advantages have been described in detail, it should be understood that various changes, substitutions and alterations can be made herein without departing from the spirit and scope of the disclosure as defined by the appended claims.

Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A simulated method for navigating surgical instrument based on tomography, comprising:

obtaining a biological stereoscopic image and inputting a parameter set of an implant to be implanted;

denoting a target position and an initial position in the biological stereoscopic image;

estimating a dimensional coordinate of a contact area of the implant and a living organism when the implant has been implanted into the living organism based on the parameter set, the target position and the initial position in the biological stereoscopic image;

obtaining a physiological data set by re-sampling corresponding to the dimensional coordinate of the implant in the living organism; wherein a tomographical physiological data is obtained according to the dimensional coordinate in the living organism, and a bone volume fraction physiological data, a volumetric bone mineral density physiological data or a blood vessel path physiological data is obtained according to the tomographical physiological data;

obtaining the dimensional coordinate of the implant and the dimensional coordinate of a contact area as a CT image for evaluating the effect after the implant has been implanted into the living organism;

setting a rigid destructive mode and a soft destructive mode in the parameter set;

when the rigid destructive mode has been set, sampling after the corresponding space in the living organism has been replaced by the implant in order to obtain the dimensional coordinate and the physiological data; and when the soft destructive mode has been set, sampling the corresponding space in the living organism in order to obtain the dimensional coordinate and the physiological data after evaluating a deformation of the biological stereoscopic image according to the parameter set.

2. The simulated method as claimed in claim 1, wherein a computed tomographical physiological data is obtained according to the dimensional coordinate in the living organism, and a bone volume fraction physiological data and a volumetric bone mineral density physiological data is obtained according to the computed tomographical physiological data.

* * * * *